United States Patent [19]

Saaski et al.

[11] Patent Number: 5,039,492

[45] Date of Patent: Aug. 13, 1991

[54] OPTICAL PH AND GAS CONCENTRATION SENSOR

[75] Inventors: Elric W. Saaski, Bothell; David A. McCrae, Seattle; James C. Hartl, Snohomish; Dale M. Lawrence, Lynnwood; Roger A. Wolthuis, Woodinville, all of Wash.

[73] Assignee: MetriCor, Inc., Woodinville, Wash.

[21] Appl. No.: 303,584

[22] Filed: Jan. 27, 1989

[51] Int. Cl.$^5$ .................. G01N 21/00; A67B 5/00; G02B 5/00

[52] U.S. Cl. .................. 422/82.09; 422/55; 422/82.05; 422/82.08; 436/136; 436/138; 436/144; 128/633; 128/634; 128/636; 356/432; 356/436; 359/839; 359/884

[58] Field of Search ............. 436/136, 138; 422/55, 422/58, 60, 82.03, 82.04, 82.05, 82.09, 56; 128/633, 634; 350/628, 642; 364/413.09

[56] References Cited

U.S. PATENT DOCUMENTS

| | | |
|---|---|---|
| Re. 31,879 | 5/1985 | Lubbers et al. . |
| 2,806,023 | 8/1957 | Wenker . |
| 3,202,652 | 9/1965 | Meininger et al. . |
| 3,446,565 | 9/1969 | Rigod . |
| 3,544,484 | 12/1970 | Roth ..................... 422/56 |
| 4,003,707 | 1/1977 | Lübbers et al. ........... 128/634 |
| 4,016,761 | 4/1977 | Rozzell et al. . |
| 4,029,597 | 6/1977 | Neisius et al. . |
| 4,118,485 | 10/1978 | Eriksson et al. . |
| 4,140,393 | 2/1979 | Cetas . |
| 4,200,110 | 4/1980 | Peterson et al. ........... 422/58 |
| 4,210,029 | 7/1980 | Porter . |
| 4,249,076 | 2/1981 | Begstrom et al. . |
| 4,275,296 | 6/1981 | Adolfsson . |
| 4,306,877 | 12/1981 | Lübbers ................. 128/633 |
| 4,307,607 | 12/1981 | Saaski et al. . |
| 4,316,388 | 2/1982 | Miller et al. . |
| 4,329,058 | 5/1982 | James . |
| 4,356,396 | 10/1982 | Ruel et al. . |
| 4,367,040 | 1/1983 | Goto . |
| 4,428,239 | 1/1984 | Johnston . |
| 4,437,761 | 3/1984 | Kroger et al. . |
| 4,446,366 | 5/1984 | Brobardh et al. . |
| 4,487,206 | 12/1984 | Aagard . |
| 4,498,004 | 2/1985 | Adolfsson et al. . |
| 4,568,518 | 2/1986 | Wolfbeis et al. ........... 422/56 |
| 4,617,608 | 10/1986 | Blonder et al. . |
| 4,678,904 | 7/1987 | Saaski . |
| 4,682,500 | 7/1987 | Kuzutaka et al. . |
| 4,780,372 | 10/1988 | Tracy et al. ............. 350/642 |
| 4,785,814 | 11/1988 | Kane .................... 128/634 |
| 4,803,049 | 2/1989 | Hirschfeld et al. ......... 128/634 |
| 4,849,172 | 7/1989 | Yafuso et al. ............. 422/56 |
| 4,851,195 | 7/1989 | Matthews et al. ......... 128/634 |

OTHER PUBLICATIONS

Silacon as a Mechanical Material, Proceeding of the IEEE, vol. 70, No. 5, May, 1982 by Kurt Peterson.

Field Assisted Glass Sealing, Electrocomponent Science & Technology, 1975, vol. 2, No. 1, pp. 45-53 by George Wallis.

Reference cited in Office Action 03/02/89-Pat. No. 4,678,904 as Pat. No. 4,628,904 (double patenting).

Primary Examiner—Robert J. Warden
Assistant Examiner—Theresa A. Trembley
Attorney, Agent, or Firm—Seed and Berry

[57] ABSTRACT

An optical pH sensor and a gas sensor utilizing the pH sensor. The pH sensor includes an indicator whose absorbance is a function of the concentration of hydronium ions in a media surrounding the indicator. Light transmitted and reflected through the indicator of the sensor undergoes an absorption that is characteristic of the concentration of the hydrogen ion. The pH sensor can be used as to sense the concenration of a gas in a sample by surrounding the indicator with a liquid or liquid-containing media that changes pH as it is exposed to the gas, and separating the indicator and liquid or liquid-containing media from the gas with a membrane that is permeable to the gas to be measured. A measuring system used with the sensors transmits coherent radiation to the sensor through an optical fiber, separates the radiation returning from the sample into two wavelength bands, and digitally samples the photocurrents produced within the two wavelength bands. A microprocessor performs ratiometric calculations to measure the pH or gas concentration.

21 Claims, 7 Drawing Sheets

OPTICAL PH AND GAS CONCENTRATION SENSOR

TECHNICAL FIELD

This invention relates to systems for sensing pH and gas concentrations, and more particularly, to an optical pH sensor for liquids and a gas concentration sensor using the pH sensor.

BACKGROUND ART

Modern-day diagnosis and treatment of patients undergoing surgery and other critically ill patients often require the measurement of blood gases. Blood gas measurement is a term that has come to stand for the measurement of $pCO_2$, $pO_2$ and pH. These blood parameters are regarded as critical measures in the clinical assessment of pulmonary and cardiovascular function.

Current hospital practice for measuring blood gases is both time-consuming and expensive. A sample of the patient's blood must be specially prepared and treated before it is sent to a dedicated blood gas analysis instrument within the hospital laboratory. While this instrument performs the blood analysis quickly, significant time delays occur in taking the sample to the analysis instrument and returning with the analysis results. Although some of the time lost by processing the blood samples at a remote location has been regained by placing blood gas analyzer instruments in or near surgical and other critical care units, the instruments are expensive and require the assignment of specially trained laboratory personnel.

A variety of methods for making bedside blood gas measurements have been proposed. The transcutaneous method, which makes blood gas measurements through the skin, is not accurate when used with adult patients, and it does not measure pH. Direct contact measurements, made by sensors placed within the vascular system or by bringing blood to sensors outside the patient's body, have also been proposed. Miniature electrochemical sensors have proven to be unstable and expensive. Miniature field-effect transistors (FETs), controlled by chemicals or ions, continue to present various developmental problems. Miniature gas chromatographs or mass spectrometers are expensive to build, service, and maintain. Some miniature optical-based systems rely on fluorescence. These systems interrogate a fluorescent dye with light at a first wavelength. The dye then emits light at a second wavelength or, in some cases, light at second and third wavelengths. Hydronium ions in a sample diffuse into the dye so that the pH of the dye becomes equalized to the pH of the sample. The intensity of the light emitted by the dye is a function of the pH of the dye. The intensity of the light emitted by the dye is thus an indication of the pH of the sample. The interrogating light for these conventional fluorescent systems must be at a short wavelength which is incompatible with solid-state light sources. Furthermore, fluorescence pH sensors are inherently inefficient since optical systems are generally capable of capturing only a small portion of the light emitted by the fluorescent dye. Fluorescence pH sensors also require optical fibers that are capable of operating over a relatively wide bandwidth. However, suitable optical fibers are difficult to produce, and they have other characteristics that limit performance. Other miniature optical systems use electromagnetic energy at other short wavelengths. These systems are not compatible with solid-state hardware.

It would be particularly useful then, to have an electro-optical pH and gas sensor that is based on changes in the absorption/transmission of specific chemical indicators that operate at longer wavelengths and that can be supported by cost-effective, solid-state electronics. Additionally, it would be useful to use such sensors for blood pH and gas measurements and to make such sensors so that they are inexpensive and thus disposable after use with a single patient.

SUMMARY OF THE INVENTION

It is an object of the present invention to provide an optical sensor for measuring the pH of a sample based on changes in the optical absorption/transmission characteristics of specific chemical indicators when exposed to the sample.

It is another object of the present invention to provide a gas concentration sensor utilizing the optical pH sensor.

It is another object of the present invention to provide a pH sensor that operates at optical wavelengths that are compatible with solid-state electronics.

It is still another object of the present invention to provide an optical measurement system for use with optical absorption/transmission sensors.

A sensor of the present invention receives radiation having predetermined color characteristics and includes an indicator chamber containing an indicator having light absorption/transmission characteristics that vary with the pH of a sample in contact with the indicator in the indicator chamber. The sample may be either a liquid or a liquid containing media, such as a solid or gas. Light from a light-measuring unit passes through the indicator and is returned to the light-measuring unit to generate a signal indicative of the pH of the sample. In one embodiment, the indicator chamber has a radiation-transmissive wall through which the incoming radiation enters the indicator chamber. The indicator chamber further has a radiation-reflective wall facing the transmissive wall on the opposite side of the indicator. The reflective wall receives the incoming radiation after it passes through the indicator, and then reflects the radiation back through the indicator to the radiation-transmissive wall where it is conveyed to a measurement device. The radiation-reflective wall has an aperture through which the sample being analyzed passes into the indicator chamber. In another embodiment, the indicator chamber has a second radiation-transmissive wall. Incoming radiation passes through the indicator to the second radiation-transmissive wall. The radiation then passes through the second radiation-transmissive wall and is conveyed to a measurement device. The first or second radiation-transmissive wall has an aperture through which the sample being analyzed passes into the indicator chamber.

The indicator may be admixed with a backfill material in the indicator chamber. Alternatively, the indicator may be a film which is affixed either to the radiation-reflective wall or to the radiation-transmissive wall. Finally, the indicator may be a film affixed to a supporting means which is transparent to the radiation.

The sensor of the present invention may be used to measure pH, and it may also be used to measure the concentration of gases in a sample. When the pH sensor is to be used as a gas sensor, a membrane that is permeable to the gas to be measured is placed over the indicator chamber to isolate the chamber from the sample. The membrane covers a wall of the indicator chamber so that the gas permeates the membrane and then moves through the aperture in the reflective wall. After the gas has permeated the membrane it reacts with a liquid or liquid-containing media in the chamber to shift the hydronium ion concentration. This, in turn, changes the absorption/transmission characteristics of the indicator within the indicator chamber. The changing absorption/transmission characteristics of the indicator allow a determination of the concentration of the hydronium ions, and the concentration of the hydronium ions depends, in turn, on the concentration of the gas. Thus, the concentration of a gas, such as $pCO_2$, can be determined.

The optical measurement system of the present invention separates the returning radiation into two spectral bands, and generates a signal representing the ratio of the total light energy contained in these two bands. Based on this ratio, a microcomputer calculates and displays the corresponding pH or concentration of a gas, such as carbon dioxide, in a sample.

Although the inventive sensor and system are described herein as primarily for measuring the pH and gas concentration in a liquid, such as blood for medical applications, it will be understood that the invention is applicable to the measurement of pH or gas concentrations in any sample for any purpose.

DETAILED DESCRIPTION OF THE INVENTION

Figure 1:
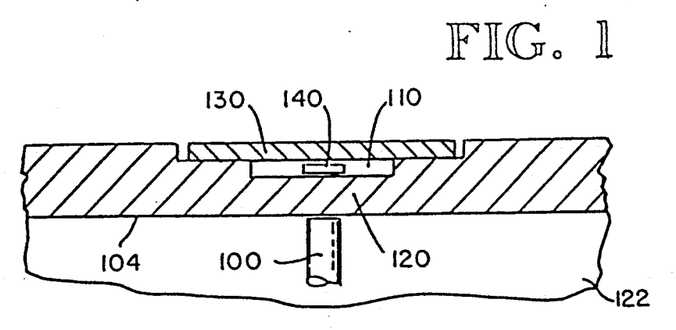
FIG. 1 is a schematic view of a pH sensor of the present invention utilizing a radiation-transmissive wall and a radiation-reflective wall in the indicator chamber.

The key features of one embodiment of the inventive gas sensor are shown in FIG. 1. The sensor receives radiation having predetermined color characteristics, typically produced by a light-emitting diode (LED) with a peak wavelength in the 600–700 nm (i.e., red) range. The sensor has a light-measuring unit operative for receiving reflected radiation and for generating a corresponding signal indicative of the concentration of the substance being analyzed. The radiation is delivered to and channeled from miniature indicator chamber 110 via optical fiber 100 in base 122. With no loss in generality, optical fiber 100 may, of course, be replaced by a bundle of fibers. The indicator chamber 110 is formed by a transparent substrate 120 preferably flush-mounted on base 122 and a radiation-reflective wall 130. In an alternative embodiment, the radiation can be supplied to the sensor from an LED built into the base 122 for the sensor and the reflected radiation can be detected by photodiodes also built into the base 122.

Figure 2:
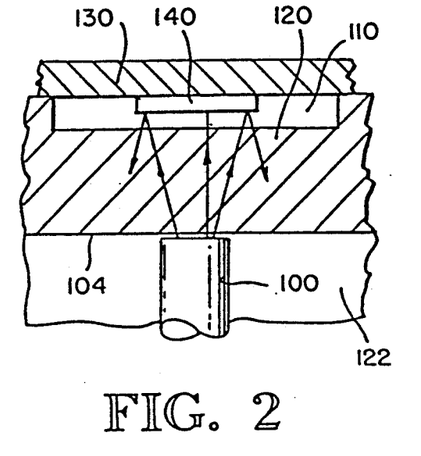
FIG. 2 is a schematic view of a pH sensor having the indicator affixed to the reflective wall.
Figure 3:
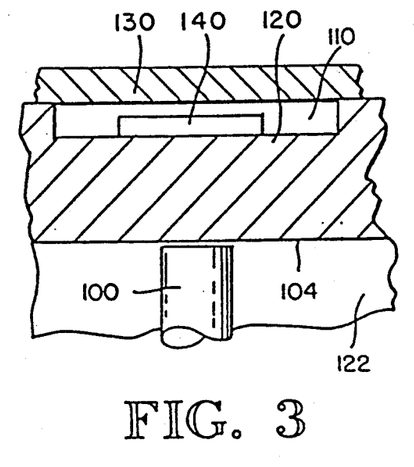
FIG. 3 is a schematic view of a pH sensor having the indicator affixed to a transmissive substrate.
Figure 4:
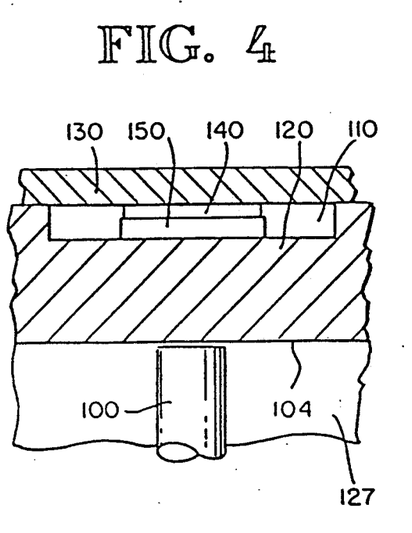
FIG. 4 is a schematic view of a pH sensor having the indicator affixed to a supporting means within the indicator chamber.
Figure 5:
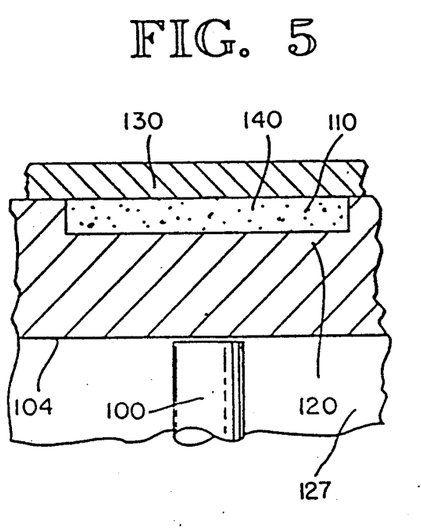
FIG. 5 is a schematic view of a pH sensor having the indicator admixed in the backfill material.

Radiation enters and exits the indicator chamber via the transparent substrate 120. The radiation-reflective wall 130 is positioned opposite the source of radiation so that the radiation is reflected back to the light-measuring unit. The sensor also contains an indicator 140 that may be positioned within indicator chamber 110 in a variety of ways. For example, as shown in FIG. 2, indicator 140 may be affixed to reflective wall 130 inside indicator chamber 110. Similarly, as shown in FIG. 3, indicator 140 may be affixed to transparent substrate 120 within indicator chamber 110. Instead of attaching indicator 140 to a wall of indicator chamber 110, indicator 140 may be affixed to a supporting means 150, such as a button, which is positioned within indicator chamber 110, as shown in FIG. 4. Finally, as FIG. 5 illustrates, the indicator 140 may be admixed with backfill material contained in indicator chamber 110.

Indicator chamber 110 is within transparent substrate 120, which is made from a transparent material capable of being formed into thin sheets, and, for example, may be plastic, Corning code 7740 glass, or quartz glass. Chamber 110 may be formed either by embossing the cavity into the surface of the transparent substrate 120 or by etching with solutions containing hydrofluoric acid. The wet chemistry methods are particularly useful in that they enable precision positioning and control of the depth of the chamber. Typical depths of the indicator chamber range from 10 to 50 microns.

For many applications, it is necessary that the sensor respond quickly to a change in its sensed environment. A basic purpose of this design is to produce low-cost yet reliable sensors having very small physical dimensions and rapid response times.

A key component of the present invention is reflective wall 130 of the indicator chamber 110. Reflective wall 130 is a mirror that reflects radiation back toward a light-measuring unit. The mirror must have high red reflectivity to maximize the returned light. The positioning of the mirror also significantly affects the ability of the sensor to track rapidly-changing gas conditions in a sample, such as blood. Decreased sensor response speed is caused by the mirror shrouding the indicator from the surrounding sample environment.

Figures 6, 7, 8:
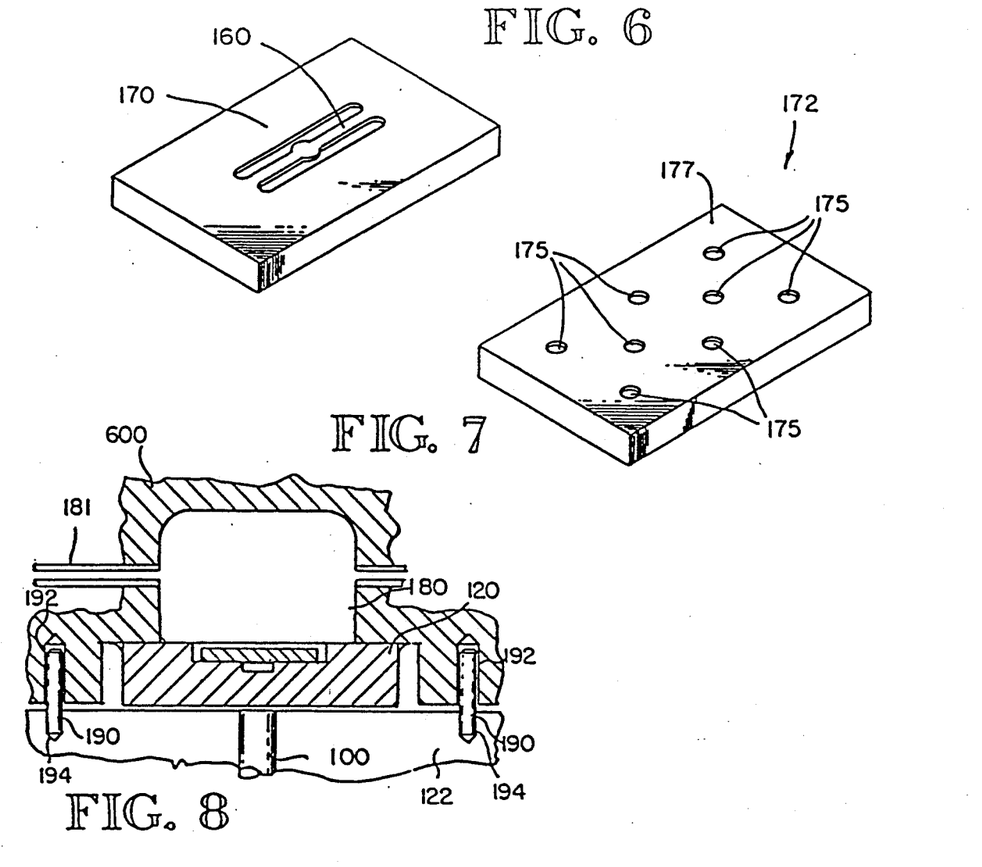
FIG. 6 is an isometric view of a mirror having two apertures.
FIG. 7 is an isometric view of a mirror having a plurality of apertures.
FIG. 8 is a schematic view of a pH sensor including a liquid sample chamber.

Two alternative mirror designs are shown in FIGS. 6 and 7. The mirror of FIG. 6 has a central reflecting bar 160 with chamber-accessing slots on each side. An additional ring of material 170 is connected to reflecting bar 160, protecting reflecting bar 160 and adding significant rigidity to the structure. This mirror shape can be generated in thin sheets of glass or plastic, or preferably, in 4-to-10 micron thick, single-crystal silicon by using standard wet chemistry micromachining methods. The mirror reflective surface is obtained by coating the polished silicon face with a highly reflective, noncorroding material, such as gold; a nonmetallic, multilayer, dielectric mirror coating may also be used. The resulting mirror is exceedingly thin, highly reflective, noncorroding, and extremely strong, this being the result of using single-crystal silicon. The use of a silicon mirror is also of significant advantage in that the lateral dimension of reflecting bar 160 can be very precisely defined and the mirror made so thin that the channels on each side of the bar do not generate a significant secondary diffusion barrier.

An alternative mirror design is shown in FIG. 7. In this approach, anisotropic silicon etching techniques are used to generate a "porous" silicon mirror 172 that has a plurality of microminiature holes 175 through the reflective silicon sheet 177. This allows more rapid communication of the gas with the indicator and results in a shorter diffusion length and faster sensor equilibration. As a general rule, an individual pore in the porous mirror should not exceed about one/eighth of the diameter of the core of the optical fiber. Typical core diameters are on the order of 0.004 inches, although core diameter of commercially available optical fibers can vary considerably from 0.004 inches. Larger pores will also work, but significant differences in reflected light levels will be found from sensor to sensor if the reflector is not essentially a homogeneous surface.

The mirror 130 is mounted directly over the indicator 110 chamber and onto the transparent substrate 120 using either anodic bonding, heat-sealing/fusion, or polymer adhesive, or by using the backfill material within the indicator chamber 110 as an adhesive. A number of mirrors may be mounted by optically or mechanically positioning them on a substrate with a corresponding number of indicator chambers therein. When in the proper position, they can be fixed very rapidly with heat-sealing or with an adhesive which hardens upon exposure to an ultraviolet light source. This will be particularly useful for mass-producing the sensors. Alternatively, they can be fixed less quickly using a conventional heat-curing adhesive.

As shown in FIG. 8, transparent substrate 120 is typically mounted in a plastic cap 600 containing a cavity 180 appropriately located so as to form a fluid (gas or liquid) sample chamber, with the substrate 120 forming one side thereof. This cavity then communicates with external liquid or gaseous samples via adhesively bonded tubes 181 mounted into the cap side walls.

Figure 9:
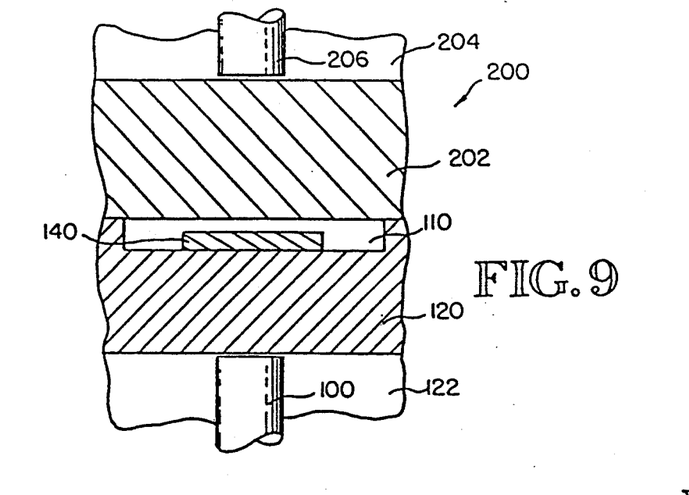
FIG. 9 is a schematic view of an alternative embodiment of the pH sensor in which radiation is transmitted through the sensor.

An alternative embodiment of the optical sensor, illustrated in FIG. 9, utilizes a second transparent substrate 202 instead of the radiation-reflective wall 130 used in the embodiment of FIGS. 1-5. The second transparent substrate 202 is mounted on a second base 204 through which extends a second optical fiber 206. The first transparent substrate 120 has a cavity formed therein to provide the indicator chamber 110 in which an indicator 140 is mounted. The transparent substrate 202 can be either porous or formed with apertures or channels to permit the gas or liquid to be sensed to pass into the indicator chamber 110.

As with the embodiment of FIGS. 1-5, the indicator chamber 110 is constructed from a transparent material capable of being formed into thin sheets, and, for example, may be plastic, Corning code 7740 glass, or quartz glass. Chamber 110 may be formed either by embossing the cavity into the surface of the transparent substance or by etching with solutions containing hydrofluoric acid. The wet chemistry methods are particularly useful in that they enable precision positioning and control of the depth of the chamber. Typical depths of the indicator chamber 110 range from 10 to 50 microns.

In operation, incoming radiation passes through the first transparent substrate 120 and the indicator 140 and into the second transparent substrate 202. The radiation passing through the second transparent substrate 202 is conveyed through the second optical fiber 206 to a measurement device. The spectral characteristic of the radiation received by the measurement unit is determined by the spectral absorbance of the indicator 140. The spectral absorbance of the indicator 140 is, in turn, determined by the hydronium ion concentration of the indicator 140. The hydronium ion concentration of the indicator reaches equilibrium with the hydronium ion concentration of the media surrounding the indicator 140. In the case of a pH sensor, the media surrounding the indicator 140 is the sample being measured. The sample may be any liquid that contains hydronium ions or any liquid-containing media, such as a gel or vapor, that contains hydronium ions. In the case of a gas sensor, the media surrounding the indicator may be a liquid or liquid-containing media that contains hydronium ions in which the concentration of hydronium ions is a function of the concentration in the media of the gas being measured.

In an alternative embodiment, the optical fiber 100 can be eliminated, and the radiation can be supplied to the sensor 200 from an LED built into the base 122. Similarly, the optical fiber 206 can be eliminated, and the radiation passing through the indicator 140 can be detected by photodiodes also built into the base 204 on which the second transparent substrate is mounted.

With reference now to FIG. 8, alignment between optical fiber 100 and sensor 140 is accomplished by locating pins 190. The locating pins 190 are received in correspondingly shaped recesses 192, 194 formed in the cap 600 and base 122, respectively. The pins 190 allow placement of transparent substrate 120 within tolerances required for fiber sensor alignment prior to adhesive bonding of wall 120 to cap 600. They also allow the use of a mirror-positioning fixture for alignment of the sensors when they are being assembled.

To maintain measurement accuracy, the indicator 140 may have to be temperature controlled. This can be accomplished by controlling the temperature of the base 122. The optical fiber 100 can be bundled with electrical conductors to form an umbilical cord that carries electrical current to resistively heat the sample base 122.

To minimize the reflection of extraneous light from the sensor, the end of the optical fiber 100 and the transparent substrate 120 must not be separated by an air gap if both are not anti-reflection coated. If any gap 04 exists between the substrate 120 and optical fiber 00, the gap can be filled with an index-matching material to minimize these unwanted reflections. Typical index-matching materials are silicone gels or polyethylene glycols having refractive indices approximately equal to that of the fiber core (typically 1.46). The latter are favored because of their nontoxicity and because their water-solubility allows the fiber base to be easily cleaned in water or alcohol. A preferred polyethylene glycol is PEG 400.

The optical fiber can alternatively be coupled to the sensor through the use of optical elements, such as lenses. This will relax the need for the optical fiber to be butted against the substrate. Optical elements may also eliminate entirely the use of optical fibers.

Sensors based on changes in absorbance are difficult to implement in medical or industrial environments because of non-sensor fluctuations in return light attributable to dirt on connector lenses or fibers, creep and drift of connector mechanical elements, and fiber cable bending. The optical interrogation technique must accurately measure changes in sensor structure absorbance while nullifying various artifacts associated with the optical fiber. A typical method of eliminating these problems consists of using two wavelengths or wavebands and rationing their relative intensities. One wavelength is chosen to have a return signal that is insensitive to sensor absorbance changes, while the second wavelength is chosen for high sensitivity to the sensor's absorbance changes. A fundamental problem with this approach is that the two wavelengths are generally so far apart that two discrete light sources are needed. This results in additional problems because the sources generally have different angular emission patterns and the fiber and connectors may not respond in the same way at these widely spaced wavelengths. Under these circumstances, the objective of error nullifying will be partially defeated.

It has been found that by using a single narrow waveband light source, and forming a ratio by splitting the spectrum of light returned from the chamber 110 into two narrow secondary wavebands, many of these problems of ratiometric detection are eliminated. This technique is described in detail in U.S. Pat. No. 4,678,904 which is incorporated herein by reference. In this concept, both secondary wavebands are attenuated significantly by the indicator, and hence the ratiometric sensitivity is reduced—but with significant gains in the areas discussed above.

The pH/gas sensors utilize an indicator whose radiation-absorption characteristics change when the indicator is exposed to a change in hydronium ion concentration. Accordingly, the pH/gas sensors involve an indicator compound whose optical absorption at some predefined wavelengths follows changes in the local pH. The indicator compound is subject to a number of constraints. The indicator compound must have its pKa within the pH measurement range of interest. The indicator must interact with light from a source compatible with the ratiometric instrumentation technique described herein; in practice, the wavelengths of interest are between 600 and 700 nm because high-power light-emitting diodes and efficient photodiodes are available at these wavelengths and because thermally stable indicators may be synthesized with strong absorbances in this waveband. The indicator must exhibit a long-term stability toward various environmental parameters. It must exhibit light stability, particularly when exposed to intense light levels in the interrogating waveband. It must also be chemically stable under the variations in temperature, pH, chemical activity, etc., expected in its operating environment. Finally, the indicator compound must be mechanically stable, that is, unable to passively diffuse from the sensor embodiment.

The numerous indicator constraints effectively eliminate all but a few groups of compounds from consideration as indicators. Some of the best compounds are known as "azo dyes" and consist of a substituted aromatic amine and a substituted coupler (containing the pH active functional group) joined by an azo linkage. These compounds are well suited for use as pH indicators in this application. Loss of a proton from the azo compound causes a large spectral change, which can be measured.

The $pK_a$ of this class of indicators may be varied over the entire pH range by varying the substituents and the type of aromatic systems. Additionally, the spectral properties may also be manipulated by varying the substituents to optimize performance at the interrogating wavelength. Compounds containing the azo functional group have been used as dyes for many years and, in general, exhibit good light stability. They also exhibit good chemical stability, except in oxidizing or reducing environments. Mechanical stability is obtained by immobilizing the indicator onto a supporting matrix. The indicator is joined to the matrix using a multifunctional "reactive compound." The reactive compound forms separate covalent bonds with both the indicator and the matrix, thus forming a chemical bridge between these two species.

The supporting matrix may be any porous material capable of supporting an aqueous environment and ion transport. Additionally, the supporting matrix needs to contain functional groups (usually nucleophilic) capable of forming bonds with the reactive group and preferably uncharged under sensor-operating conditions. A substrate of a transparent cellulose film, such as cellophane, can be used.

Figure 10A:
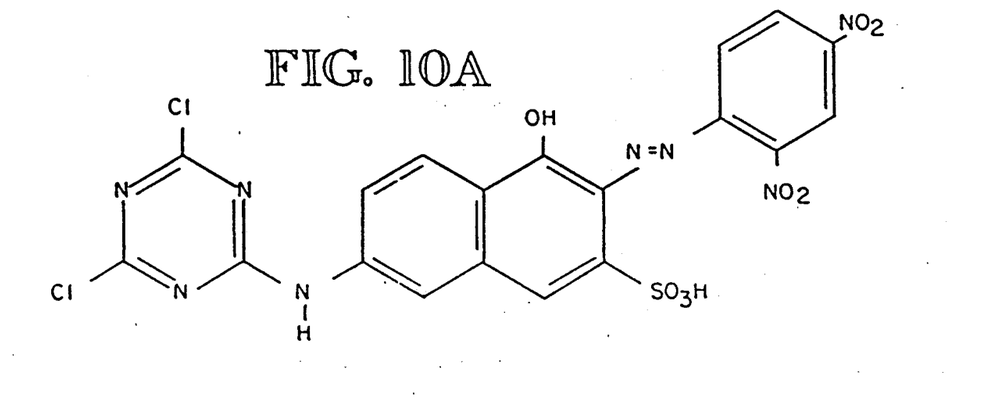
FIG. 10a represents the structure of a first preferred indicator for the pH sensor.
Figures 10B, 13:
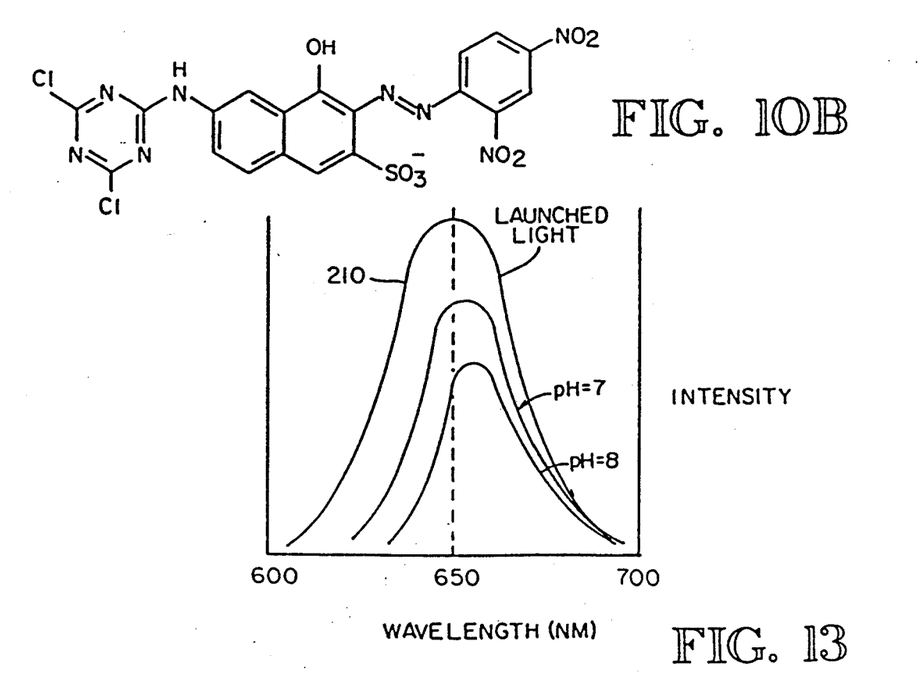
FIG. 10b represents the structure of a second preferred indicator for the pH sensor.
FIG. 13 is a plot of the return light spectra of the pH sensor as a function of wavelength for various values of pH using the first preferred indicator.
Figure 10C:
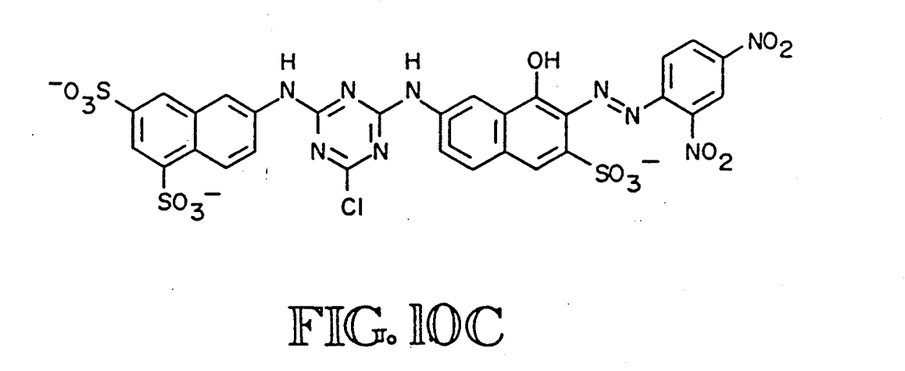
FIG. 10c represents the structure of a third preferred indicator for the pH sensor.

One specific sensor embodiment developed measures changes in the absorbance of an azo indicator compound as a function of pH. For maximum sensitivity, one of the indicator's wavelengths of absorbance at half-peak value should approximately match the interrogating light sources's spectral midpoint, or the spectral midpoint should approximately coincide with the dye's isobestic point 700. The pH range desired for medical applications is from 6.8 to 7.8, implying that the $pK_a$ for the indicator should be near 7.3. Preferred indicators for the sensors are shown in FIGS. 10a, 10b and 10c. The reactive group used for immobilization of the indicator on the supporting matrix is based on cyanuric chloride.

Figure 11A:
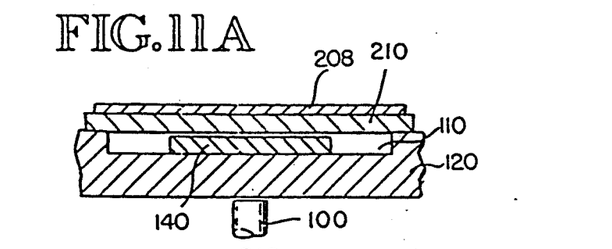
FIGS. 11A, 11B and 11C are schematic views of preferred embodiments of a gas sensor utilizing the pH sensor of the present invention.
Figure 11B:
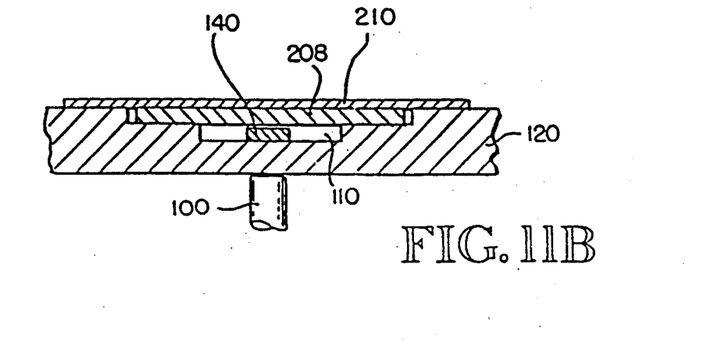

The preferred indicator in FIG. 10a has a peak spectral absorbance wavelength, Smax, at 604 nm and a wavelength at half-peak value, $S_{\frac{1}{2}}$, at 640 nm with $pK_a$ at 7.1. The second preferred indicator in FIG. 11b has $S_{max}$ also at 604 nm and an $S_{\frac{1}{2}}$ at 640 nm with $pK_a$ at 7.3. The third preferred indicator in FIG. 10c has a peak spectral absorbance at 610 nm and a $S_{\frac{1}{2}}$ at 660 nm with $pK_a$ at 7.9. The indicator is immobilized in cellulose using standard reactive dying techniques. The attachment of ionizeable molecular groups such as sulphonic acid groups to the molecule, as in the third compound, is an extremely useful method for precisely manipulating the pH response of the pH-responsive segment of the molecule, particularly in semipermeable substrates such as cellulose. Both the pH operating span and $pK_a$ can be selected in this way. The immobilized indicator has an extended usable range of pH 5 to pH 9. When immobilized in commercial cellulose film, the indicators exhibit bathochromic shifts that are useful in terms of bringing their spectra into better coincidence with several commercially available, high-intensity, 640–700 nm light sources. For the compound in FIG. 10a, the $S_{max}$ is then 618 nm and $S_{\frac{1}{2}}$ is 663 nm with $pK_a$ at 7.0.

For the compound in FIG. 10b, the $S_{max}$ is 626 nm and $S_{\frac{1}{2}}$ is 670 nm with $pK_a$ at 7.3. For the compound in FIG. 10c, the peak spectral absorbance is 628 nm and $S_{\frac{1}{2}}$ is 675 nm with $pK_a$ at 7.7. Other compounds that are useful as indicators are combinations of the couplers 6-amino-4-hydroxy-2-naphthalene sulfonic acid, 7-amino-4-hydroxy-2,7-naphthalene disulfonic acid with the amines 2,4-dinitroaniline, 5-nitro-2- aminothiazole, 2-cyano-4-nitroaniline, 2-amino-5-nitro benzotrifluoride, 4-amino, 3-nitrobenzotrifluoride, and 6-cyano-2,4-nitroaniline. The resultant azo indicators may be chemically bound to the substrate with cyanuric chloride, substituted cyanurates, and 2,3-chloro-6-chloro-carbonylquinoxaline. Also acceptable as alternative matrix materials are glycerolsubstituted porous glass, cross-linked poly(vinylalcohol), cellulose beads, cross-linked agarose, cross-linked dextran, hydroxylated acrylate polymers, and other hydrophilic polymers.

The measurement of gas concentrations is based on variations of one technique. For example, when $CO_2$ dissolves in aqueous solution, it reacts with the aqueous solution to produce various carbonate species through a series of linked equilibria. These species are predominantly charged; the pH of the aqueous solution changes, reflecting these new conditions of charge neutrality and equilibrium. If, then, an aqueous solution is isolated from the larger environment by a $CO_2$-permeable membrane, and if the pH of the aqueous solution can be determined, then a means of measuring $CO_2$ concentrations is available. Normally, the isolated aqueous solution contains a dilute concentration of an alkali metal carbonate, in equilibrium with its solid precipitate, which shifts the sensor's pH operating point to match the indicator's pH-sensitive range and increases the sensitivity and stability of the sensor. The concentration of other gases can be measured in a similar manner. Although an aqueous solution, such as water, is preferred as the media surrounding the indicator, any liquid or liquid-containing media may be used as long as it contains hydrogen ions, and the hydrogen ion concentration varies as the liquid absorbs the gas to be sensed. The liquid-containing media may be liquid in a solid, such as a gel, or liquid in a gas, such as a vapor.

The pH indicator for the gas sensor described previously (immobilized on a polar hydrophilic matrix, such as cellophane) is isolated from the external environment by an ionophobic, gas-permeable membrane constructed from various poly(siloxanes). The membrane should be ionophobic so that ions in the sample containing the gas to be measured do not pass directly through the membrane into the media surrounding the indicator. Instead, the pH of the media surrounding the indicator should be determined solely by the concentration of the gas in the media. The matrix may be soaked in a sodium bicarbonate solution to provide increased sensitivity and stability. Alternatively, the matrix may be saturated with a moderately insoluble carbonate salt precipitate, such as $CaCO_3$ or $MgCO_3$. When a salt of appropriate solubility is used, the $CO_2$-sensitive hydrogen ion equilibrium can be matched to the indicator's $pK_a$ and optimum sensitivity achieved. The incorporation of a moderately insoluble carbonate precipitate also provides a buffer-like stabilization of the pH operating point that is needed due to the small size of the device; otherwise, adventitious acid could cause the sensor to drift severely.

The indicator used in the pH sensors and in the pH/gas sensors is thin, preferably punched from a 25-micron thick cellophane film that has been previously dyed with the desired hydronium ion indicator. The indicator is covalently bound to the cellophane film.

A punch for generating small, right circular cylindrical sensor buttons can be made of stainless steel capillary tube that has been electropolished at its end. The electropolishing process paradoxically results in a very sharp cone end edge that is ideal for cleanly piercing the cellophane film. The inner diameter of the tube used is approximately the same as the desired button diameter, i.e., 0.006 to 0.012 inch. The tube outer diameter is not critical.

Figure 18:
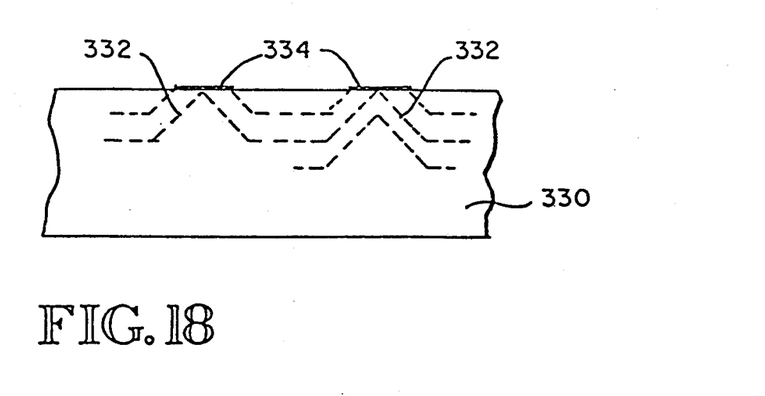
FIG. 18 is a schematic cross-sectional drawing showing the etching of a punch to produce the sensor indicator.
Figure 19:
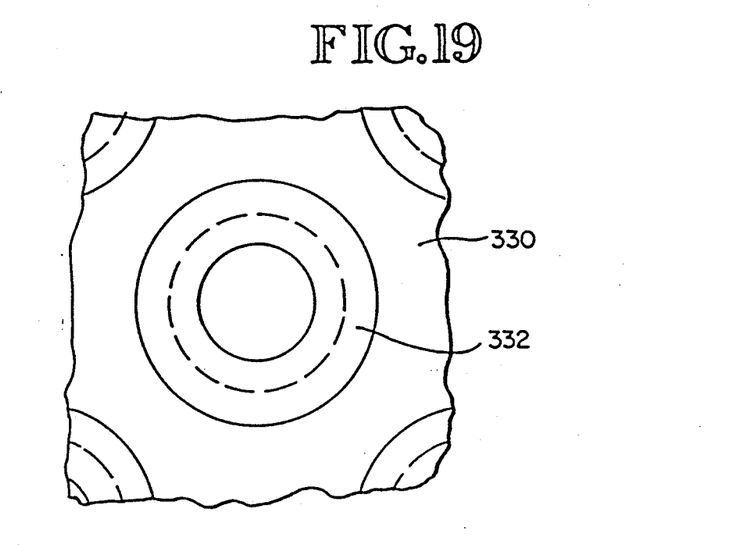
FIG. 19 is a plan view of one of the punches shown in FIG. 18.

A second punch is shown in FIGS. 18 and 19. This punch is made by photo-masking a hard yet etchable material mask 334, such as quartz, so that an array of etch-protected annular rings 332 is generated on the surface of substrate 330. When placed in an etching bath such as hydrofluoric acid, the exposed areas are etched downward into the substrate and laterally under mask 334. If the substrate is removed from the etchant when the laterally moving edges 332 just meet, a surface is thereby formed that is composed of a plurality of sharp knife-edges. When this surface is pressed with sufficient force against a cellophane film, the knife-edges punch through the film and produce a large number of buttons simultaneously.

The buttons intended for use in a pH sensor are stored in distilled water. The buttons intended for use in a $pCO_2$ sensor are treated in one of two ways, both of which help to maintain the pH operating point of the buttons. In one, the $pCO_2$ button is stored directly in a sodium bicarbonate solution of appropriate concentration until removed for use. In the other, the $pCO_2$ button is infused with solid carbonate through one of several different precipitation techniques and then stored in saturated carbonate solution until removed for use. Solid carbonates used are $CaCO_3$ and $MgCO_3$. The buttons for use in pH or $pCO_2$ sensors are placed into cylindrical, flat-bottomed chambers that approximate the hydrated button diameter. For pH, a gold-plated mirror, such as that shown in FIGS. 6 and 7, is glued onto the top of the chamber, effectively holding the button in the cavity while at the same time providing a highly reflective surface for the incoming radiation.

The indicator chamber will, in a blood gas application, contain whole blood. Whole blood has substantial optical activity in the red and near infrared and must be excluded from the optical path. This is done by etching the chamber to a depth such that once the indicator button swells on exposure to water contained in the blood, the button is lightly squeezed between the chamber bottom and the mirror crossbar. This seals the top and bottom surfaces of the button to the mirror and cavity bottom, respectively, and prevents blood from flowing into the optical path. Alternatively, a thin layer of hydrophilic gel may be used on the top and bottom surfaces to index match as well as exclude red blood cells.

Figure 11C:
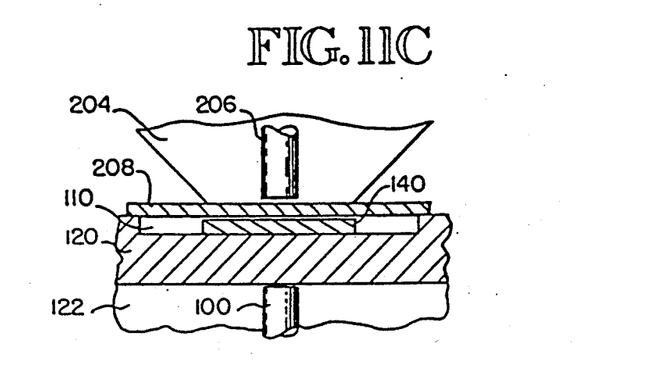

In the case of the indicator chamber for a gas sensor, the need for a squeeze fit is not critical. However, the indicator and surrounding media for a gas sensor must be ionically isolated from the sample containing the gas to be measured. As mentioned above, ionic isolation is provided by using a gas-permeable membrane that is ionophobic so that ions cannot pass directly from the sample to the media surrounding the indicator. Isolating the indicator from the external ionic environment thus allows the absorption spectra to change only as the result of gaseous interchanges that change pH conditions within the media surrounding the indicator. In the one embodiment, illustrated in FIG. 11A, a mirror 210 is placed over the indicator chamber 110 and aligned so that it will be directly over the interrogating light beam. A transparent, gas-permeable, ionophobic membrane 208 is then placed over mirror 210. This combination is then heated in an inert gas to 190–200 degrees centigrade and a voltage of 1000–3000 volts applied between the top of the membrane and a metallic plate that the sensor base is resting on. The combined effects of temperature and applied voltage smooth out irregularities in the film, and firmly seal the membrane to the quartz substrate and mirror. A membrane of choice is General Electric MEM 213 polycarbonate silicone copolymer, 25 microns thick. In a second embodiment, illustrated in FIG. 11B, a transparent, gas-permeable, ionophobic membrane 208 is mounted onto the first transparent substrate 120, and the mirror 210 sealed over the top in the manner previously indicated, using the mirror as the topmost electrode. In a third embodiment (not shown), the sensor button is potted in a silicone rubber that also holds the mirror in position and provides the requisite ionic isolation. Finally, in a fourth embodiment, illustrated in FIG. 11C, a gas-permeable, ionophobic membrane 208 is placed over the second transparent substrate 202 of a transmission-type sensor.

The optical and stability properties of the gas sensor may also be enhanced by using an ionophobic oil as a sensor button encapsulant. This is achieved by constructing a narrow trench etched in the substrate and extending from the sensor cavity to the exterior. Satisfactory trench width and depths are in the range of 1 to 50 microns. After a thin polymer cover has been bonded over the top of the cavity, as in FIGS. 11A and 11B, wicking action is used to flow oil into the cavity via the trench. Since the oil is ionophobic, ionic isolation has not been compromised. By appropriate selection of an oil for refractive index and viscosity, the sensor's optical clarity can be enhanced and allowance made for expansion and contraction of the sensor button during changes in external osmotic conditions without a build-up of stresses and pressures within the cavity. A suitable oil is silicone PSO49 manufactured by Petrarch Chemical Co.

This viscous, hydrophobic liquid sealing procedure also prevents high external pressures from deforming the mirror/sensor assembly since it provides hydrostatic pressure neutralization between the cavity and exterior environments.

Figure 12:
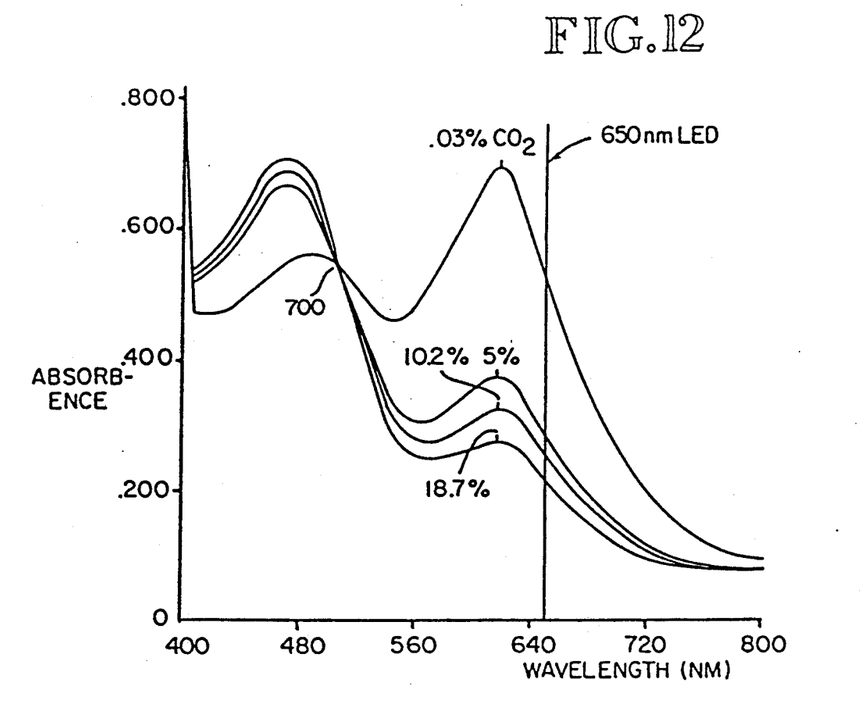
FIG. 12 is a plot of the absorption spectra of the pH sensor as a function of wavelength for various values of $CO_2$ using the first preferred indicator.

The spectral response of a typical pH or gas sensor is shown in FIG. 12. From this example, it is clear that choosing to operate the sensor at a peak wavelength of between about 630 and 670 nm, or at the isobestic point 700, will provide a sensor whose response is a monotonic function of the pH or concentration of gas in a liquid. While operation centered around the isobestic point will provide the largest change in return spectrum for a given change in hydrogen ion concentration, it is generally preferable to operate on the long-wavelength spectrum segment so that solid state light sources can be utilized.

FIG. 13 shows that, for a given launched light spectrum whose intensity is shown by curve 210, the absorption pH sensor described above produces spectral responses whose overall levels are functions of the pH of the sample. For this sensor, the higher the pH of the sample, the higher the absorption of light over the source's bandwidth. By using the narrow-band spectral splitting technique described herein, it is clear that when operating on the far red half of the absorbance spectrum that the light source's shorter wavelength secondary waveband will always be absorbed more than the longer wavelength waveband. However, the waveband photocurrent ratio will not be constant, but will change smoothly in correspondence with indicator absorbance variations.

Figure 15:
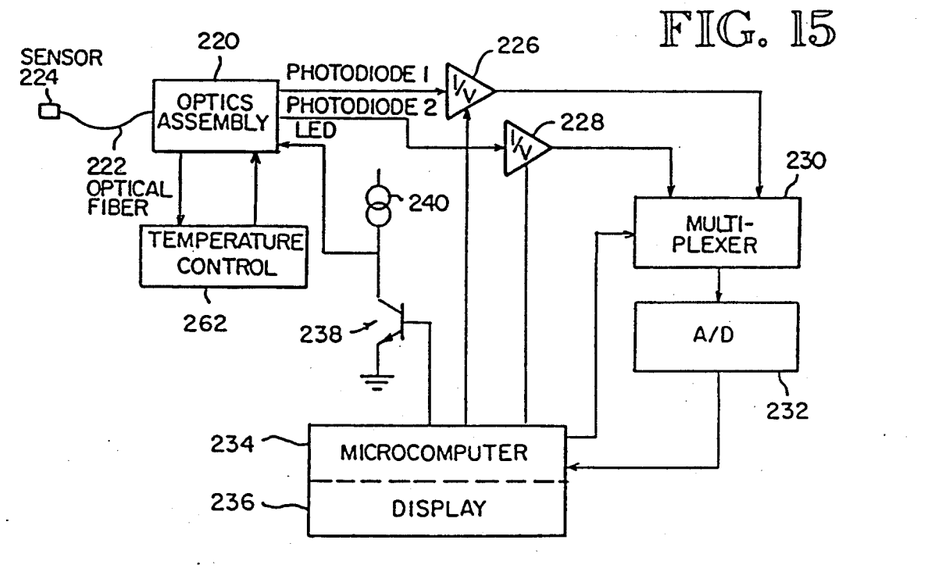
FIG. 15 is a schematic diagram of a system for measuring pH of a sample or the concentration of a gas.

A schematic diagram of the measurement system for use with pH and gas concentration sensors is shown in FIG. 15. Optics assembly 220 produces light at a characteristic band of wavelengths and sends that light over optical fiber 222 to sensor 224. In response to the concentration of the measured blood gas in the blood sample, sensor 224 produces an altered spectral signal that is returned over optical fiber 222 to optics assembly 220. Optics assembly 220 produces two photodiode signals and sends them to transimpedance amplifiers 226 and 228. These transimpedance amplifiers transform the photocurrent signals produced by the photodiodes to voltage signals, which, in turn, are input to multiplexer 230. The multiplexer alternately samples the voltage signals produced by the transimpedance amplifiers 226 and 228 to produce an analog signal that is sent to analog-to-digital (A/D) converter 232. Microcomputer 234 is programmed to receive the digitized signals from A/D converter 232 and to calculate the ratio of the two photocurrents and determine the corresponding blood gas concentration from this ratio. The result is then displayed on display 236. It can also be output in other forms, such as RS-232, analog voltages or currents, or other digital communications formats.

Figure 16:
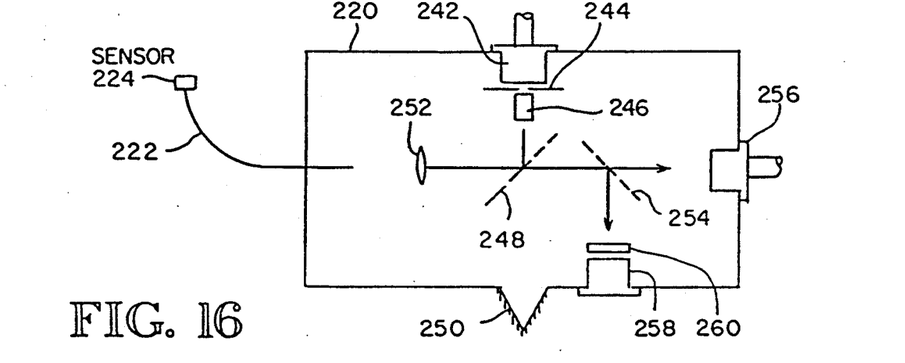
FIG. 16 is a schematic view of the optics assembly of the system in FIG. 15.

A schematic diagram of optics assembly 220 is shown in FIG. 16. The intensity of the light produced by LED 242 is determined by the current delivered from constant current source 240, depending upon the current passing through transistor 238 under the control of microcomputer 234 (see FIG. 15). LED 242 can, for example, be chosen to produce light with a peak wavelength in the range of 600 to 700 nm, using commercially available, high-intensity red sources. The light from LED 242 passes through a pinhole aperture 244 and a ¼ pitch SELFOC lens 246 before reaching neutral beam splitter 248. Pinhole aperture 244 minimizes stray light in optics assembly 220, and SELFOC lens 246 collimates the light from pinhole aperture 244. A portion of the light striking neutral beam splitter 248 passes through to light dump 250, which can, for example, constitute a wedge-shaped cavity that has been coated with an absorptive dye. Since it is important that the light dump does not reflect light back into the optics assembly, the light dump must be very effective. A reflectivity of less than $1(10^{-5})$ is desirable.

The collimated light that is reflected by neutral beam splitter 248 passes through lens 252, which focuses the pinhole image onto the end of optical fiber 222. The alignment of lens 252 with the end of optical fiber 222 is important. Therefore, one possible configuration of these optical components is to place the lens and the end of the optical fiber into a separate assembly that allows them to be disconnected from the optics assembly. The light reflected from the lens back into the optics assembly should be minimized. Accordingly, the lens can be given an antireflection coating or highly curved surfaces. In this way, light reflected from lens 252 does not return along the same optical path as the beam formed by light returning from sensor 224 on optical fiber 222. It is also necessary to control reflections from the fiber end. To achieve this, the fiber end may be given an antireflection coating, or the lens may be designed so that the fiber directly contacts the surface of the lens and reflections are minimized by use of index-matching fluids or gels.

This lens/fiber interface is available as a purchased fiber-optic connector, for example, Deutsch series 3000 fiber connector.

The light launched into the optical fiber 222 travels to the sensor 224 and passes through the indicator-containing media to a reflector. The light is then reflected back through the media, and a portion enters the fiber. The fraction of launched light which is returned is determined primarily by three factors. The first factor is the distance from the end of the fiber to the reflecting surface of the sensor. As shown in FIG. 2, as the fiber-to-reflecting surface distance increases, the diameter of the reflected beam also increases and the fraction of light reentering the fiber decreases. It is, therefore, important to minimize the substrate thickness consistent with the limits of mechanical strength. The second loss mechanism is absorption at the reflective mirror. The reflecting surface should have high reflectivity over the wavelengths of interest, 600 to 700 nm, and be compatible with blood. Gold is a suitable material. Light losses due to this mechanism may be somewhat spectrally dependent, but should not vary with either time or environment. The third loss mechanism is absorption in the indicator media. The absorption losses are spectrally dependent and the spectral dependence of the absorption is determined by the value of the parameter being measured, as shown in FIG. 12.

Returning to FIG. 16, the light returning from sensor 224 along optical fiber 222 passes through lens 252 and on to beam splitter 254. The beam splitter may be a dichroic beam splitter or may be a neutral beam splitter. If beam splitter 254 is a dichroic beam splitter, the spectral content of the light which is transmitted through the beam splitter is different from the spectral content of the light that is reflected by the beam splitter. If beam splitter 254 is a neutral filter beam splitter, the spectral content of the transmitted and reflected light is identical. Photodiode 256 produces a photocurrent that measures the intensity of the light transmitted by beam splitter 254, while photodiode 258 measures the intensity of the light reflected by beam splitter 254. If beam splitter 254 is a neutral filter beam splitter, the reflected light can be passed through a filter 260 before reaching photodiode 258. In this case, the ratio of the photocurrents produced by photodiodes 258 and 256, respectively, is the ratio of the intensity of the returned light in the waveband defined by filter 260 to the intensity of the light produced over the entire spectrum returned from sensor 224.

If, on the other hand, beam splitter 254 is a dichroic mirror, a selected portion of the LED's waveband is transmitted to photodiode 256, while the remainder of the waveband is reflected to photodiode 258. Other spectral splitting techniques that can be used in optics assembly 220 include diffraction gratings, prisms, and combinations of all of these methods. Since the ratio of the photocurrents produced by photodiodes 256 and 258 measures only the relative magnitudes, this ratio is insensitive to connector and bending losses related to optical fiber 222.

The light spectrum of an LED is temperature-dependent. Therefore, unless a technique for measuring the spectrum is included in the optics assembly, it is necessary to maintain LED 242 at a constant temperature. In addition, the spectral characteristics of absorptive filters and dichroic filters are temperature-dependent. It is possible to monitor the wavelength distribution of the LED using filters identical to those used to analyze the light returned from the sensor. If this is done, the effect of temperature on filter characteristics can be largely compensated and the effect of temperature on the LED corrected by microcomputer 234 (in FIG. 15).

Alternatively, it is possible to control the temperature of the entire optics assembly 220. This simplifies the optics assembly as well as the system software. The temperature in optics assembly 220 is maintained with a thermoelectric heater/cooler and a semiconductor temperature sensor which communicate with temperature control 262. Temperature control 262 can, for example, implement a proportional integral (PI) or proportional integral differential (PID) control circuit.

Figure 14:
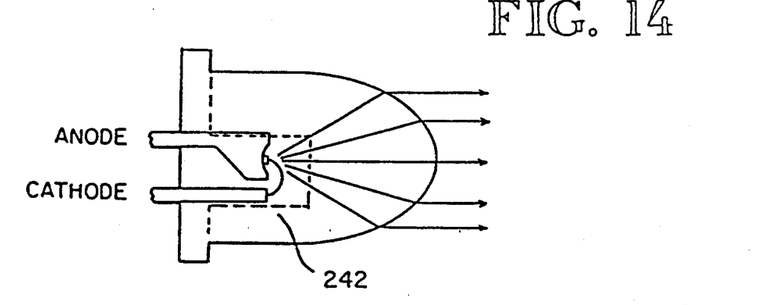
FIG. 14 is a schematic view of the structure of an LED light source.

LED 242 may be mounted in a plastic package. In order to reduce the thermal resistance between the LED die and the optics assembly, the package of a conventional LED is machined as shown by the dotted lines in FIG. 14. This allows direct contact to the anode and greatly reduces the thermal resistance between the die and the interior of the optics assembly, and fluctuations therein.

Microcomputer 234 can also control the gain of transimpedance amplifiers 226 and 228. Reference currents can be injected into the transimpedance amplifiers under the control of microcomputer 234 to measure the relative gain ratio between the amplifiers in order to compensate for electronics drift.

Figure 17:
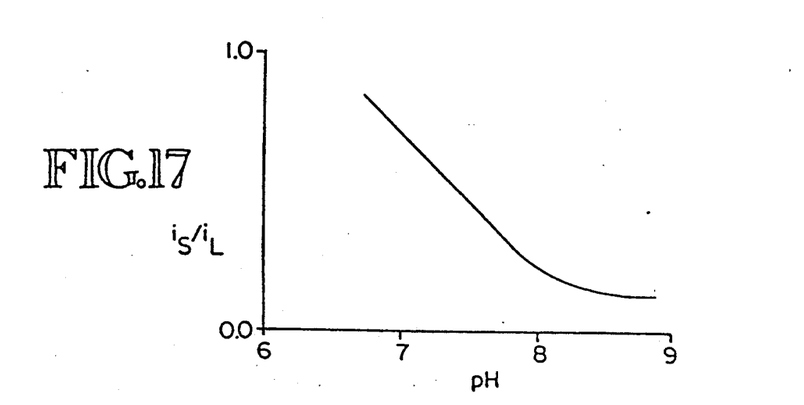
FIG. 17 is a plot of the photocurrent ratio produced by the optics assembly of FIG. 16, shown as a function of pH.

FIG. 17 presents representative data for the ratio of short-pass wavelength photocurrent to the long-pass wavelength photocurrent as a function of pH. As can be seen, the ratio is monotonic and approximately linear over the pH range of physiological interest, i.e., 6.8 to 7.8. Since pH is a logarithmic function of gas concentration, photocurrent ratio is approximately logarithmic for gas sensors.

Although the total amount of light sent to the sensor is relatively small, the intensity is quite high; therefore, the possibility of photodegradation of the sensor indicator exists. In order to limit the degradation of the indicator, LED 242 in optics assembly 220 is kept off until a sensor reading is taken. When taking a sensor reading, the LED is pulsed on, and, after a fixed time interval, the A/D conversions are made by A/D converter 232 and the desired ratio computed by microcomputer 234. The LED is in a thermal transient after being turned on, and, therefore, it is necessary that the time interval between turning on the LED and reading the photocurrents be reproducibly controlled. It has been determined that a delay between 0.01 and 1.0 second reduces the criticality of the time interval but does not cause undue degradation of the sensor indicator and eliminates possible reduction of the life of the LED.

It is thus seen that the inventive optical sensors of the present invention provide an accurate measurement of the pH of a sample, and they can be used to implement a variety of sensors for measuring the concentration of a gas. Further, the sensors are readily adaptable to commonly used solid-state light sources.

We claim:

1. A sensing system for measuring the concentration of a gas in a sample, comprising:
    a source of radiation having predetermined spectral characteristics;
    a substrate defining an indicator chamber cavity containing a liquid medium or liquid-containing medium that undergoes a change in hydrogen ion concentration as it absorbs the gas to be measured;
    a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane; and
    indicator means contained in said medium so that said radiation passing into said cavity passes through said indicator means, said indicator means having radiation absorption/transmission characteristics that vary as a function of the hydrogen ion concentration of said medium, said indicator means being an azo dye having absorption/transmission characteristics that are sensitive to the concentration of hydronium ions in said medium, said azo dye being 6 (3',5'-dichloro-2',4',6'triazinylamino)-3-(2'',4''-dinitrophenyl-1''-azo)-4-hydroxynaphthalene-2-sulfonic acid, sodium salt, having the formula:

2. A sensing system for measuring the concentration of a gas in a sample, comprising:
    a source of radiation having predetermined spectral characteristics;
    a substrate defining an indicator chamber cavity containing a liquid medium or liquid-containing medium that undergoes a change in hydrogen ion concentration as it absorbs the gas to be measured;
    a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane; and
    indicator means contained in said medium so that said radiation passing into said cavity passes through said indicator means, said indicator means having radiation absorption/transmission characteristics that vary as a function of the hydrogen ion concentration of said medium, said indicator means being an azo dye having absorption/transmission characteristics that are sensitive to the concentration of hydronium ions in said medium, said azo dye being 7 (3',5'-dichloro-2',4',6'-triazinylamino)-3-(2'',4''-dinitrophenyl-1''-azo)-4-hydroxynaphthalene-2-sulfonic acid, sodium salt, having the formula:

3. A sensing system for measuring the concentration of a gas in a sample, comprising:
    a source of radiation having predetermined spectral characteristics;
    a substrate defining an indicator chamber cavity containing a liquid medium or liquid-containing medium that undergoes a change in hydrogen ion concentration as it absorbs the gas to be measured;
    a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane; and
    indicator means contained in said medium so that said radiation passing into said cavity passes through said indicator means, said indicator means having radiation absorption/transmission characteristics that vary as a function of the hydrogen ion concentration of said medium, said indicator means being an azo dye having absorption/transmission characteristics that are sensitive to the concentration of hydronium ions in said medium, said azo dye being 6-amino-1,3-naphthalene-disulfonic acid/$K_2CO_3$, having the formula:

4. A sensing system for measuring the concentration of a gas in a sample, comprising:
a source of radiation having predetermined spectral characteristics:
a substrate defining an indicator chamber cavity containing a liquid medium or liquid-containing medium that undergoes a change in hydrogen ion concentration as it absorbs the gas to be measured;
a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane;
indicator means contained in said medium so that said radiation passing into said cavity passes through said indicator means, said indicator means having radiation absorption/transmission characteristics that vary as a function of the hydrogen ion concentration of said medium;
measurement means for measuring radiation, said means being operative to receive said radiation passing through said indicator means and generate a corresponding signal indicative of the concentration of the gas in said sample; and
means for transmitting said radiation from said source of radiation to said indicator chamber, and from said indicator chamber to said measurement means, said means for transmitting including a radiation-transmissive wall receiving said radiation from said source of radiation through said transmitting means, and a radiation-reflective wall facing the transmissive wall for reflecting radiation transmitted through said indicator means from said radiation-transmissive wall whereby radiation from said source of radiation is transmitted through said indicator means, reflected from said radiation-reflective wall back through said indicator means to said radiation-transmissive wall and through said coupling means to said measurement means, said radiation-reflective wall being formed by a mirror having an aperture to allow said gas to pass through said mirror into said indicator chamber.

5. The sensing system of claim 4 wherein said aperture is in the form of a pair of elongated parallel slots in said mirror forming a reflecting bar therebetween.

6. The sensing system of claim 4 wherein said mirror is fabricated by wet chemistry micromachining of a sheet of reflective material.

7. The sensing system of claim 4 wherein said mirror has formed therein a plurality of microminiature aperture.

8. The sensing system of claim 4 wherein said mirror is formed from a sheet of thin film porous media coated with a reflective substance.

9. A sensing system for measuring the concentration of a gas in a sample, comprising:

a source of radiation having predetermined spectral characteristics:
a substrate defining an indicator chamber cavity containing a liquid medium or liquid-containing medium that undergoes a change in hydrogen ion concentration as it absorbs the gas to be measured;
a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane;
indicator means contained in said medium so that said radiation passing into said cavity passes through said indicator means, said indicator means having radiation absorption/transmission characteristics that vary as a function of the hydrogen ion concentration of said medium;
ionophobic oil encapsulating said indicator means to enhance the optical and stability properties of said sensing system;
measurement means for measuring radiation, said means being operative to receive said radiation passing through said indicator means and generate a corresponding signal indicative of the concentration of the gas in said sample; and
means for transmitting said radiation from said source of radiation to said indicator chamber, and from said indicator chamber to said measurement means.

10. A sensing system for measuring the pH of a sample, comprising:
a source of radiation having predetermined spectral characteristics; and
indicator means communicating with said sample so that ions within said sample can interact with said indicator means, said indicator means having radiation absporption/transmission characteristics that vary as a function of the pH of the sample; said indicator means being an azo dye having absorption/transmission characteristics that are sensitive to the concentration of hydronium ions in said sample, said azo dye being 6 (3',5'-dichloro-2',4',6'-triazinylamino)-3-(2'',4''-dinitrophenyl-1''-azo)-4-hydroxynaphthalene-2-sulfonic acid, sodium salt, having the formula:

11. A sensing system for measuring the pH of a sample, comprising:
a source of radiation having predetermined spectral characteristics; and
indicator means communicating with said sample so that ions within said sample can interact with said indicator means, said indicator means having radiation absorption/transmission characteristics that vary as a function of the pH of the sample; said indicator means being an azo dye having absorption/transmission characteristics that are sensitive to the concentration of hydronium ions in said sample, said azo dye being 7-(3',5'-dichloro-2',4',6'-triazinylamino)-3-(2",4" -dinitrophenyl-1"-azo-4-hydroxynaphthalene-2-sulfonic acid, sodium salt, having the formula:

12. A sensing system for measuring the pH of a sample, comprising:
a source of radiation having predetermined spectral characteristics; and
indicator means communicating with said sample so that ions within said sample can interact with said indicator means, said indicator means having radiation absorption/transmission characteristics that vary as a function of the pH of the sample; said indicator means being an azo dye having absorption/transmission characteristics that are sensitive to the concentration of hydronium ions in said sample, said azo dye being 6-amino-1,3-naphthalene-disulfonic acid/$K_2CO_3$, having the formula:

13. A sensing system for measuring the pH of a sample, comprising:
a source of radiation having predetermined spectral characteristics; and
indicator means communicating with said sample so that ions within said sample can interact with said indicator means, said indicator means having radiation absorption/transmission characteristics that vary as a function of the pH of the sample; said indicator means being disposed on a substrate defining an indicator chamber cavity communicating with said sample, said indicator chamber including a radiation-transmissive wall receiving said radiation from said source of radiation through said optical means and coupling radiation to said measurement means through said optical means, and a radiation-reflective wall facing the transmissive wall for reflecting radiation transmitted through said indicator means from said radiation-transmissive wall whereby radiation from said source of radiation is transmitted through said indicator means, reflected from said radiation-reflective wall back through said indicator means to said radiation-transmissive wall and through said optical means to said measurement means, said radiation-reflective wall being formed by a mirror having an aperture to allow said sample to pass through said mirror into said indicator chamber.

14. The sensing system of claim 13 wherein said aperture is in the form of a pair of elongated parallel slots in said mirror forming a reflecting bar therebetween.

15. The sensing system of claim 13 wherein said mirror is fabricated by wet chemistry micromachining of a sheet of reflective material.

16. The sensing system of claim 13 wherein said mirror is formed from a sheet of thin film porous media coated with a reflective substance.

17. The sensing system of claim 13 wherein said mirror has formed therein a plurality of microminiature apertures.

18. A sensing system for measuring the pH of a sample, comprising:
a source of radiation having predetermined spectral characteristics; and
indicator means communicating with said sample so that ions within said sample can interact with said indicator means, said indicator means having radiation absorption/transmission characteristics that vary as a function of the pH of the sample; said indicator means being disposed on a substrate defining an indicator chamber cavity communicating with said sample, said indicator chamber including a radiation-transmissive wall receiving said radiation from said source of radiation through said optical means and coupling radiation to said measurement means through said optical means, and a radiation-reflective wall facing the transmissive wall for reflecting radiation transmitted through said indicator means from said radiation-transmissive wall whereby radiation from said source of radiation is transmitted through said indicator means, reflected from said radiation-reflective wall back through said indicator means to said radiation-transmissive wall and through said optical means to said measurement means, and a layer of hydrophilic gel placed between said indicator means and said radiation-transmissive wall and between said indicator means and said radiation-reflective wall, said gel index matching said indicator means to said radiation-transmissive and radiation-reflective walls and excluding said liquid sample from the path of said radiation through said indicator chamber cavity.

19. A sensing system for measuring the concentration of a gas in a sample, comprising:
a source of radiation having predetermined spectral characteristics over a band of wavelengths;
a substrate defining an indicator chamber cavity containing a liquid medium or liquid-containing medium that undergoes a change in hydrogen ion concentration as it absorbs the gas to be measured;
optical means for transmitting said radiation into said indicator chamber cavity;
a membrane enclosing an opening in said indicator chamber cavity to retain said medium in said indicator chamber cavity, said membrane being permeable to the gas to be measured so that said gas can be absorbed into said medium to change the pH of said medium when said sample contacts said membrane;
indicator means contained in said medium so that said radiation passing into said cavity passes through said indicator means, said indicator means having radiation absorption/transmission characteristics that vary as a function of the hydrogen ion concentration of said medium and that change differently in upper and lower spectral bands of said radiation;
measurement means for measuring radiation, said means being operative to receive said radiation passing through said indicator means and to generate a signal representative of the ratio of the spectral content of the reflected light in the upper spectral band of wavelengths to the spectral content of the reflected light in the lower spectral band of wavelengths, thereby providing a signal indicative of the concentration of the gas in said sample; and
means for transmitting said radiation from said source of radiation to said indicator chamber, and from said indicator chamber to said measurement means.

20. The sensing system of claim 19 wherein said indicator means has a spectral response of a periodic nature with a plurality of relative minima and maxima values, and wherein said upper and lower spectral bands of said wavelengths are located between adjacent minima and maxima values.

21. The sensing system of claim 19 wherein said indicator means has a plurality of spectral responses curves all of which pass through a common isobestic point and wherein said band of wavelengths is centered around said isobestic point.

* * * * *

UNITED STATES PATENT AND TRADEMARK OFFICE
CERTIFICATE OF CORRECTION

PATENT NO. : 5,039,492

DATED : August 13, 1991

INVENTOR(S) : Elric W. Saaski et al.

It is certified that error appears in the above-identified patent and that said Letters Patent is hereby corrected as shown below:

In column 15, claim 1, line 47, please delete "6  (3',5'-dichloro-2',4',6'triazinylamino) and substitute therefor --6-(3',5'-dichloro-2',4',6'-triazinylamino)--.

In column 16, claim 2, line 23, please delete "7  (3',5'-dichloro-2',4',6'-triazinylamino)" and substitute therefor --7-(3',5'-dichloro-2',4',6'-triazinylamino)--.

In column 18, claim 10, line 54, please delete "6  (3',5'-dichloro-2',4',6'-triazinylamino) and substitute therefor --6-(3',5'-dichloro-2',4',6'-triazinylamino)--.

In column 19, claim 11, line 14, after "azo" please insert -- ) --.

Signed and Sealed this

Twenty-second Day of December, 1992

*Attest:*

DOUGLAS B. COMER

*Attesting Officer*   *Acting Commissioner of Patents and Trademarks*